US00PP31196P3

(12) United States Plant Patent
Fernández

(10) Patent No.: US PP31,196 P3
(45) Date of Patent: Dec. 10, 2019

(54) ***RUBUS* PLANT NAMED 'EMR 20172'**

(50) Latin Name: ***Rubus idaeus* hybrid**
Varietal Denomination: emr 20172

(71) Applicant: East Malling Services Ltd, Kent (GB)

(72) Inventor: Felicidad Fernández, Maidstone (GB)

(73) Assignee: EAST MALLING SERVICES, LTD, Kent (GB)

( * ) Notice: Subject to any disclaimer, the term of this patent is extended or adjusted under 35 U.S.C. 154(b) by 0 days.

(21) Appl. No.: 15/932,075

(22) Filed: Jan. 29, 2018

(65) Prior Publication Data

US 2018/0220570 P1 Aug. 2, 2018

(30) Foreign Application Priority Data

Jan. 31, 2017 (QZ) ..... PBR 20170262

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
See application file for complete search history.

(56) References Cited

PUBLICATIONS

UPOV hit on *Rubus* plant named, 'Emr 20172', QZ PBR 20170262, filed Feb. 1, 2017.*

* cited by examiner

*Primary Examiner* — Anne Marie Grunberg
(74) *Attorney, Agent, or Firm* — Penny J. Aguirre

(57) ABSTRACT

A new cultivar of *Rubus idaeus* hybrid plant, 'emr 20172', characterized by its attractive, pale red, bright blunt conical shaped fruit that is well displayed and easy to detach (even in the pink stage), excellent shipping properties and shelf-life that make an ideal variety for large-scale commercial production as a primocane fruiting cultivar, its moderately vigorous primocanes that are held erect with developed lateral branches, its pines and thorns that are not prominent enough to interfere with picking and/or pruning, its berries with excellent eating quality both at harvest and after shipping, its berries that are sweet, fairly aromatic, firm, and juicy with a good balance of sugar and acid, and its early to very early fruiting on primocanes in late summer to early autumn and is not suitable for double cropping.

2 Drawing Sheets

Botanical classification: *Rubus idaeus* hybrid.
Cultivar designation: 'emr 20172'.

BACKGROUND OF THE INVENTION

The present invention relates to a new and distinct cultivar of raspberry plant, botanically thought to be of hybrid origin with *Rubus idaeus* and other species in its ancestry. 'emr 20172' and will be referred to hereinafter by its cultivar name, 'emr 20172'. 'emr 20172' is a new raspberry plant grown for fruit production.

'emr 20172' arose from an on going breeding program conducted by the Inventor in East Malling, Kent, United Kingdom. The objectives of the breeding program are to develop new cultivars of *Rubus* with outstanding fruit quality in primocane fruiting varieties.

'emr 20172' was discovered by the Inventor as a chance seedling in summer of 2009 in a trial bed that had been planted with seeds of unknown parentage. 'emr 20172' underwent further trials in the United Kingdom and Spain from 2010 to 2017 to verify its unique and stable characteristics.

Asexual propagation of the new cultivar was first accomplished by the Inventor by root cuttings in East Malling, Kent, United Kingdom in winter of 2009. Asexual propagation of the new cultivar by root cuttings, stem cuttings, and tissue culture using meristem tissue has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'emr 20172' as a new and unique cultivar of *Rubus*.

1. 'emr 20172' exhibits attractive, pale red, bright blunt conical shaped fruit that is well displayed and easy to detach (even in the pink stage).
2. 'emr 20172' exhibits excellent shipping properties and shelf-life that make an ideal variety for large-scale commercial production as a primocane fruiting cultivar.
3. 'emr 20172' exhibits moderately vigorous primocanes that are held erect with developed lateral branches.
4. 'emr 20172' exhibits spines and thorns that are not prominent enough to interfere with picking and/or pruning.
5. 'emr 20172' exhibits berries with excellent eating quality both at harvest and after shipping.
6. 'emr 20171' exhibits berries that are sweet, fairly aromatic, firm, and juicy with a good balance of sugar and acid.

7. 'emr 20172' exhibits an early to very early fruiting on primocanes in late summer to early autumn and is not suitable for double cropping.

'emr 20172' can be compared to the cultivars 'Kwell' (not patented) and 'Imara' (not patented). 'Kwell' and 'Imara' are similar to 'emr 20172' in fruiting on primcanes, and in having similar plant habits, similar yields, blunt conical shaped fruit, excellent commercial quality and good shelf lives. 'Kwell' differs from 'emr 20172' in having a cropping time that starts at least 2 to 3 weeks later, in also producing fruit on floricanes, and in having leafets that are not held flat and darker fruit that is less sweet at harvest. 'Imara' differs from 'emr 20172' having a cropping time that starts at least 1 week later, in having canes that have more thorns that are darker in color, in also producing fruit on floricanes, in having darker fruit that is less sweet at harvest.

BRIEF DESCRIPTION OF THE DRAWINGS

The accompanying colored photographs illustrate the overall appearance and distinct characteristics of the new *Rubus*. The photographs were taken of plants about 3 years in age as grown in peat based trough containers in tunnels in East Malling, Kent, United Kingdom.

The photograph in FIG. 1 provides a view of the fruiting canes of 'emr 20172' showing berries at different stages of maturation.

Figure 1:
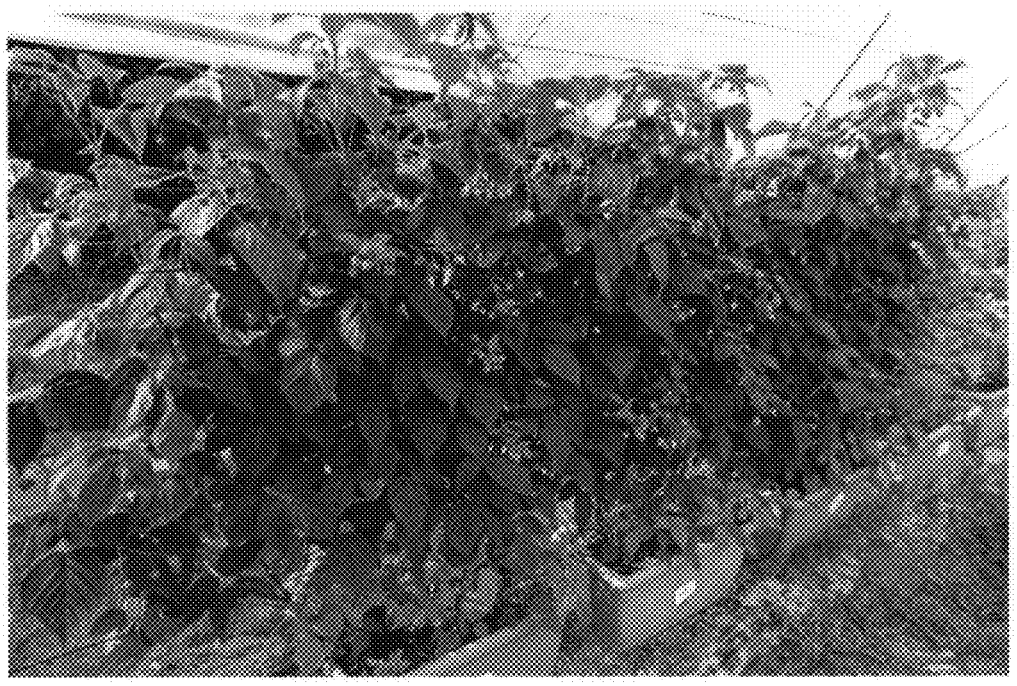
Figure 2:
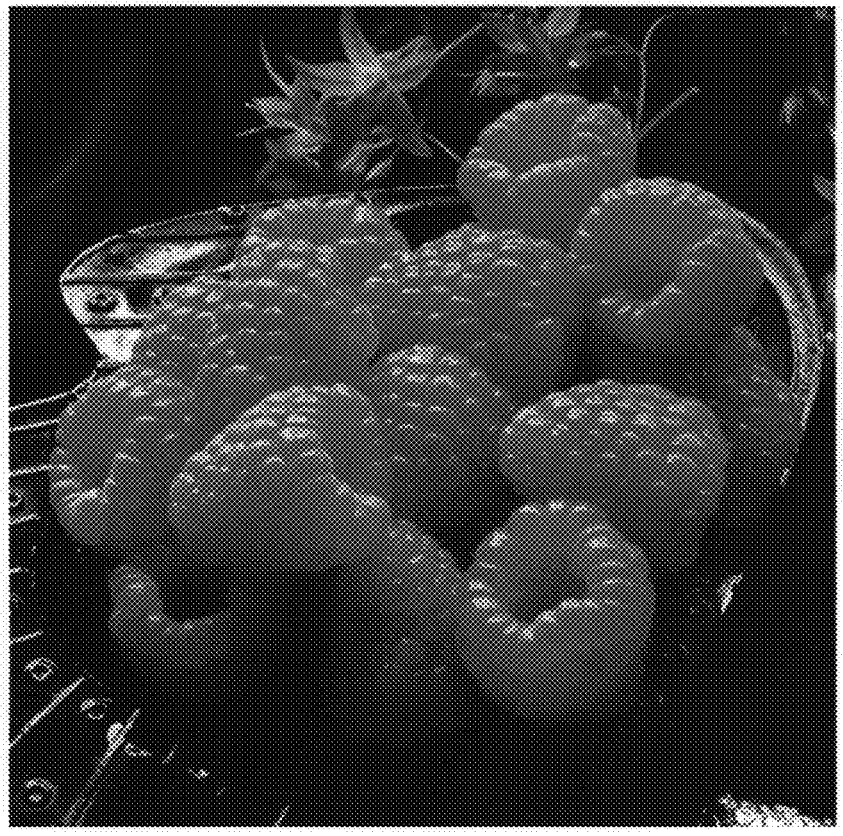

The photograph in FIG. 2 provides a close-up view of the fruit of 'emr 20172'.

Figure 3:
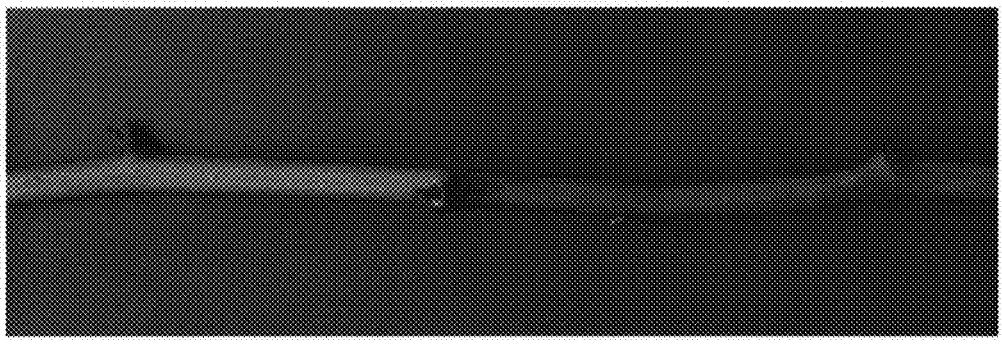

The photograph in FIG. 3 provides a view of a dormant cane of 'emr 20172'.

The colors in the photographs are as close as possible with the photographic and printing technology utilized. The colors in the photograph may differ slightly from the color values cited in the detailed botanical description, which accurately describe the colors of the new *Rubus*.

DETAILED BOTANICAL DESCRIPTION OF THE PLANT

The following is a detailed description of 2 year-old plants of the new cultivar as grown under Spanish tunnels in trough containers in East Malling, Kent, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used. This variety is primarily grown as a primocane so the descriptions are focused on the year cane toward the end of the summer when in full production.

General description:

*Blooming period*.—As a primocane; early season; flowering from July to late October in Southern England.

*Plant type*.—Fruit producing perennial.

*Plant habit*.—Upright and not overly vigorous with well-developed laterals and branches.

*Height and spread*.—Can vary significantly depending on pedoclimatic conditions, irrigation management and fertilizer regime, for plants grown on a coarse peat-based substrate in a typical year the primocane canes can reach up to 1.5 m height, spreading of around 1 to 1.5 m, heat or water stress can cause the primocanes to stop growing at around 1 m and advance the cropping season.

*Hardiness*.—This trait has not been fully characterized in a range of cold weather climates but the plants can successfully grow in England (U. K. Hardiness Zone 8) and areas of central Europe (U. K. Hardiness Zone 7).

*Diseases and pests*.—No resistance to pests or diseases has been observed and intermediately susceptible to *Verticillum* wilt (caused by *Verticillium dahliae*) in field conditions of Southern England.

*Root description*.—Fibrous and vigorous.

*Branching habit*.—Freely branching.

*Propagation*.—Root cuttings (preferred), stem cuttings or tissue culture.

*Root development*.—1.5 to 2.5 weeks to initiate roots under mist, an average of 2 months to fully develop as a young plant from a rooted cutting.

*Growth rate*.—Moderate.

Cane description (new growth; primocanes, mature canes; floricanes):

*Cane size*.—An average can vary with the season, typically 1.4 to 1.6 m in length but up 1.8 m in length has been observed, an average of 6.8 mm in width at mid stem.

*Stem color*.—The new canes are pale green as they grow (145B to 145D), towards the end of the growing season they mature to a darker color at the base 166A, that fades into lighter greener shades toward the top of the cane (145B to 145C), the dormant cane is primarily 166B in color and typically under conventional polythene tunnels the canes develop only a mild blush of 184A that can be more pronounced under different growing conditions.

*Stem surface*.—New growth; semi-glabrous with some (usually sparse) spines and thorns, spine color 183B.

*Stipules*.—2 per petiole, slightly pubescent but primarily smooth, an average of 7.8 mm in length, linear in shape, color 144B.

Foliage description:

*Time of vegetative bud burst*.—In the floricane, bud burst is typically in early to mid May but it can vary significantly from year to year.

*Leaf shape*.—Ovate in overall form.

*Leaf division*.—5 leaflets (occasionally 3).

*Leaf attachment*.—Petiolate.

*Leaf orientation*.—Primarily flat (occasionally pendant).

*Leaf size*.—An average of 18.3 cm in length and 18 cm in width.

*Leaf quantity*.—An average of 27 per cane.

*Internode length*.—An average of 4.4 cm.

*Leaflet shape*.—Ovate.

*Leaflet base*.—Terminal leaflets; cordate, lateral leaflets; ovate to oblique.

*Leaflet apex*.—Acute to acuminate.

*Leaflet venation*.—Pinnate, color primarily matches leaf color.

*Leaflet margins*.—Doubly serrate.

*Relative position of lateral leaflet*.—Slightly overlapping.

*Profile of leaflet cross-section*.—Flat to slightly convex.

*Leaflet arrangement*.—One terminal and 1 to 2 lateral pairs.

*Leaflet attachment*.—Sessile, occasionally half stalked or stalked.

*Leaflet surface*.—Upper and lower surface slightly rugose.

*Leaflet color*.—Young leaf: upper surface 144A, lower surface 144A; Mature leaf: upper surface 137D, lower surface 146B.

*Leaflet size*.—Terminal; an average of 11 cm in length and 7.8 cm in width, lateral; an average of 9 cm in length and 4.7 cm in width.

*Petioles*.—Round in shape, an average of 4.3 cm in length and 1.9 mm in width, color 145C, surface pubescent and without spines and prickles.

*Rachis*.—Round in shape, an average of 3.1 cm in length and 1.4 mm in width, color; sun exposed upper surface 145A and suffused with 173A, shaded lower surface 145C, all surfaces pubescent and without spines and prickles.

Inflorescence description:

*Inflorescence*.—Raceme, an average of 11 cm in length (from base of petiole), average of 2 cm in length (from base of rachis) and 1.6 cm in width under first bud.

*Rachis* (*peduncle*).—Round to oval in shape, color 145A, almost glabrous surface with a tiny amount of downy hair and occasional spines and prickles.

*Pedicels*.—Oval in shape, an average of 3.75 cm in length and 1.15 mm in width, color 146D, surface glabrous without spines and prickles.

*Flower buds*.—Triangular in shape with a flat wide bottom and apex narrowing to a point, up to 6.3 mm in width and 8.5 mm in length, color 144B.

*Flower type*.—Spreading calyx with a center of a ring of numerous upright stamens and with numerous pistils in the center, petals are quickly shed upon opening.

*Flower number*.—An average of 7.6 per raceme.

*Flower size*.—Average of 7.3 mm in depth and 1.7 cm in diameter.

*Sepals*.—Five, an average of 7.6 mm in length and 4.6 mm in width, base aristate, apex aristate, both surfaces have downy hair and are spineless.

*Petals*.—Five, dropped at the fruit maturity stage, an average of 7.39 mm in length and 3.08 mm in width, linear in shape with a rounded apex and oblong base, glabrous on upper and lower surfaces, thin, color in flowering to fruit maturity; 155B and changing to N155C, 36D, 55B, and finally 54C.

*Receptacle*.—An average of 9.8 mm in diameter and 17.1 mm in depth, color 158A.

*Androecium*.—An average of 94 stamens that form a concentric ring in an average 9.4 mm in diameter, inserted into calyx at base, about 5.19 mm in length, filament color 158A, pollen was not observed.

*Gynoecium*.—An average of 110 pistils, styles are an average of 3.4 mm in length and 155B in color, stigmas are very small and ovate in shape.

Fruit description:

*Fruit number*.—An average of 10 per fruiting lateral.

*Fruit size*.—An average 6.7 g (range 5.0-9.5 g).

*Fruit shape*.—Aggregate fruit is blunt conical.

*Drupelets*.—An average of 102 per aggregate fruit, globose in shape, firm, presenting a small dent in the middle, an average of 4.82 mm in diameter and height, color when mature; 45C, surface is glossy, style and stigma; persistent at maturity.

*Persistence of bracts*.—Persistent.

*Fruit size as aggregate*.—2.2 cm in length and 2.19 cm in width on average although a range of variability is possible in this trait depending on the period of record and whether terminal fruit are part of the average or recorded separately.

*Receptacle*.—It is conical to blunt conical in shape and persistent at harvest, fleshy, size varies with individual fruit size, generally creamy white in color (155B to 155C) but showing varying shades of pink in fully ripe or overripe fruit (becoming N155B with various amounts shading of 41C.

*Fruit maturity date*.—Late summer to early fall as an early to very early primocane variety in England.

*Seed*.—Kidney shape, 1 per drupelet, 2.3 mm in length, 1.3 mm in width, 164D in color.

*Cropping frequency*.—Annually, produced on same year cane (primocanes).

*Flavor*.—Sweet, juicy.

*Brix*.—Under our growing conditions, 9.5-10°.

*Fruit weight*.—Average of 6.7 g.

*Shelf life*.—When harvested optimally, fruits can be transported and kept in chilled conditions without noticeable deterioration for 6 or more days after picking.

It is claimed:

1. A new and distinct cultivar of *Rubus idaeus* hybrid plant named 'emr 20172' as herein illustrated and described.

* * * * *